(12) United States Patent
Rosenberg (10) Patent No.: US 7,183,454 B1
(45) Date of Patent: Feb. 27, 2007

(54) MULTIPURPOSE DYNAMIC OCCLUSIVE DRESSING

(75) Inventor: Lior Rosenberg, Omer (IL)

(73) Assignee: L.R. R&D, Ltd., Omer (IL)

( * ) Notice: Subject to any disclaimer, the term of this patent is extended or adjusted under 35 U.S.C. 154(b) by 0 days.

(21) Appl. No.: 09/424,499

(22) PCT Filed: May 25, 1998

(86) PCT No.: PCT/IL98/00238

§ 371 (c)(1),
(2), (4) Date: Feb. 28, 2000

(87) PCT Pub. No.: WO98/53778

PCT Pub. Date: Dec. 3, 1998

(30) Foreign Application Priority Data

May 26, 1997  (IL) .................................. 120910

(51) Int. Cl.
*A61F 13/00* (2006.01)
*A61F 13/02* (2006.01)

(52) U.S. Cl. .................... 602/43; 602/41; 602/42; 602/53; 602/54; 604/307

(58) Field of Classification Search ............ 602/41–59; 128/888, 889; 604/307, 308, 305; 606/213, 606/214, 215, 216
See application file for complete search history.

(56) References Cited

U.S. PATENT DOCUMENTS

| | | | | |
|---|---|---|---|---|
| 2,273,873 A | * | 2/1942 | Klein | |
| 3,339,546 A | * | 9/1967 | Chen | |
| 3,814,095 A | * | 6/1974 | Lubens | 604/307 |
| 4,641,643 A | * | 2/1987 | Greer | 602/57 |
| 4,738,257 A | * | 4/1988 | Meyer et al. | 602/48 |
| 4,969,881 A | | 11/1990 | Viesters | |
| 5,109,874 A | * | 5/1992 | Bellingham et al. | 128/888 |
| 5,437,683 A | * | 8/1995 | Neumann et al. | 606/151 |
| 5,662,625 A | * | 9/1997 | Westwood | 604/305 |

FOREIGN PATENT DOCUMENTS

| | | |
|---|---|---|
| EP | 0 117714 A | 9/1984 |
| WO | 85-01439 A | 4/1988 |
| WO | 96 15745 A | 5/1996 |

* cited by examiner

*Primary Examiner*—Danton D. DeMille
*Assistant Examiner*—Annette Dixon
(74) *Attorney, Agent, or Firm*—Browdy and Neimark, PLLC (57) ABSTRACT

Occlusive dressing system, which comprises an endless, elongated, flexible, adhesive barrier, adapted to be arranged in a closed configuration, whereby to bound and define a surface area, and an impermeable sealing film adapted to overlie said surface area and to isolate it from the environment, when superimposed to said barrier arranged in said configuration, said barrier forming a gas-tight seal with said sealing film when the two are applied to and pressed against one another. A spreading mechanism that alows a single person to spread the sealing film over the occluding barrier and to detach the film from the main roll and ports (inlet and outlet) that can be placed across the barrier or the occluding film.

18 Claims, 12 Drawing Sheets

MULTIPURPOSE DYNAMIC OCCLUSIVE DRESSING

FIELD OF THE INVENTION

This invention relates to an occlusive dressing system, for use in skin therapy.

BACKGROUND OF THE INVENTION

The goal of any medical dressing is to promote the natural healing and/or regeneration processes by providing the tissues with the optimal conditions for the healing phenomenon.

The dressings may be divided into two general groups:
(a) open dressings, where a rather free exchange of matter (e.g. gases, fluids, germs) may take place between the wound and the external environment; and
(b) occlusive dressing, where an impermeable barrier separates the wound and its immediate environment from the external environment and the atmosphere.

Basically, the occlusive dressings are made of impermeable films and the peripheries of their undersurface are coated with a thin layer of pressure sensitive, biocompatible adhesive. The dressings may contain various medicines in a form of thick gels, ointments or granules or even the film itself may be impregnated or medicated with the desired medicine. The open dressings are mostly made of porous or fibrous materials such as knotted fiber, gauze or non-woven cottons, wool or other natural or synthetic substances. Their contact with the wound surface may produce favorable healing conditions depending on the dressing nature and the exchange equilibrium with the external environment.

Obviously the occlusive dressings offer a better opportunity to control the wounds immediate environment, and to protect it from harmful external factors. The drawbacks of these dressings are their cost and complexity of application.

PCT Application No. WO 85/01439 discloses a protective waterproof covering for an animal body. The covering is a thin, flexible, lightweight waterproof material such as polyethylene and is shaped to conform to that part of the body to be covered. The covering has means for attachment to the body. The coverings may be attached using pressure sensitive adhesive applied about the edge region of the covering or by using elasticized bands.

EP-A 0 117 714 A2 discloses a device for protecting a wound comprising a pad of skin-protective and skin-curative adhesive material to which is secured a foldable sheet of liquid-impermeable material of larger area than the pad, marginal areas of said sheet being provided with a sealing means, and said sheet being located and dimensioned so that said sheet when folded over on itself is sealed in liquid-tight fashion around its edges to define a compartment.

PCT Application No. WO 96/15745 discloses a wound treatment device for attachment to a patient's skin surface which comprises a wound attachment portion lying in contact with a patient's skin surface, a wound treatment portion defining a wound treatment area on the patient's skin surface and a transition portion for coupling the attachment portion to the wound treatment portion which includes a membrane connected to the attachment portion proximate to the patient's skin surface and connected to a standoff included in the wound treatment portion.

DE-A-1963375 discloses a touch-free protection system for sensitive skin areas, characterized in that a distancing material comprising a gap or gaps is applied by using its self-adhesive property between a cover and a skin region.

PCT Application No. WO 85/01439 discloses a protective waterproof covering for an animal body. The covering is a thin, flexible, lightweight waterproof material such as polyethylene and is shaped to conform to that part of the body to be covered. The covering has means for attachment to the body. The coverings may be attached using pressure sensitive adhesive applied about the edge region of the covering or by using elasticized bands.

EP-A 0 117 714 A2 discloses a device for protecting a wound comprising a pad of skin-protective and skin-curative adhesive material to which is secured a foldable sheet of liquid-impermeable material of larger area than the pad, marginal areas of said sheet being provided with a sealing means, and said sheet being located and dimensioned so that said sheet when folded over on itself is sealed in liquid-tight fashion around its edges to define a compartment.

PCT Application No. WO 96/15745 discloses a wound treatment device for attachment to a patient's skin surface which comprises a wound attachment portion lying in contact with a patient's skin surface, a wound treatment portion defining a wound treatment area on the patient's skin surface and a transition portion for coupling the attachment portion to the wound treatment portion which includes a membrane connected to the attachment portion proximate to the patient's skin surface and connected to a standoff included in the wound treatment portion.

DE-A-1963375 discloses a touch-free protection system for sensitive skin areas, characterized in that a distancing material comprising a gap or gaps is applied by using its self-adhesive property between a cover and a skin region.

Two inherent problems of the present occlusive dressings are:
(a) the difficulty in occluding efficiently the irregular body's topography especially where large areas are involved; and
(b) the limitation in changing the nature of the dressing's contents and the occluded wound's micro environment without disrupting or replacing the entire dressing.

This is the reason why the existing occlusive dressings are rather small and specific, and are designed to be used only in small and usually chronic wounds such as pressure sores, legs ulcers and stomal wounds. At present, in addition to the traditional cotton gauze dressings, there exists a plethora of other kinds of dressings made of natural or synthetic materials each designed to provide a specific factor or component to the healing process. Even if we were to assume that each dressing's claims are truly fulfilled, the complex healing process and its ever-changing demands require a close monitoring and selection of a new appropriate dressing from the ever-growing dressing's armamentarium to satisfy the new demands.

It is a purpose of this invention to overcome the drawbacks of existing occlusive dressing systems.

In particular, it is a purpose of this invention to provide an occlusive dressing system which can conform to and occlude any area of the body of a patient regardless of his size, shape, location or skin irregularities.

It is another purpose of this invention to provide such a system which may contain any medicament, other desired substances or a specific physical environment in the form of solids, gels, ointments, liquids, gases or electrical and magnetic fields.

It is a further purpose of the invention to provide such a system the contents of which may be changed as desired and thus increase, decrease, change or replace, without disrupting or changing the dressing itself.

It is a still further purpose of this invention to provide such a system which permits the physical features of the dressing to be designed to promote specific biological activities in the occluded micro-environment of the affected area.

It is a still further purpose of the invention to provide such a system which permits to control and modify the environment occluded and contained by the dressing without its disruption.

Other purposes and advantages of the invention will appear as the description proceeds.

SUMMARY OF THE INVENTION

The occlusive dressing system according to the invention comprises an endless, elongated, flexible, adhesive barrier, adapted to be arranged in a closed configuration, whereby to bound and define a surface area, and an impermeable sealing film adapted to overlie said surface area and to isolate it from the environment, when superimposed to said barrier arranged in said configuration, said barrier forming a gas-tight seal with said sealing film when the two are applied to and pressed against one another.

The term "endless", with reference to the adhesive barrier, is to be construed as meaning that the barrier is substantially longer than required for making any single dressing. The condition that the barrier is "adhesive" means that its outer surface is adhesive and sealing. Therefore, the barrier may be made of adhesive and sealing material, e.g., an adhesive plastic or adhesive gel or paste, or it can be made of a flexible material that is not adhesive, but is covered with an adhesive and sealing layer. The two juxtaposed ends of the barrier will adhere to one another either end-to-end or side-to-side as the case may be, and thus the barrier may be gas-tight.

In a preferred form of the invention, the dressing system of the invention comprises means for providing, when open, a communication between the external environment and the space underlying said sealing film. Said communication means preferably comprise at least one valve or port connected to conduit means which have an inlet/outlet in said space underlying said sealing film and an inlet/outlet outside said space.

Optionally, said dressing system may further comprise a stabilizing and carrier matrix and/or a releasing system, as hereinafter defined and explained.

BRIEF DESCRIPTION OF THE DRAWINGS

In the drawings:

FIGS. 5a and 5b illustrate in schematic perspective view an adapter for applying a valve to a dressing according to an embodiment of the invention, wherein:

DETAILED DESCRIPTION OF THE INVENTION

Figure 1:
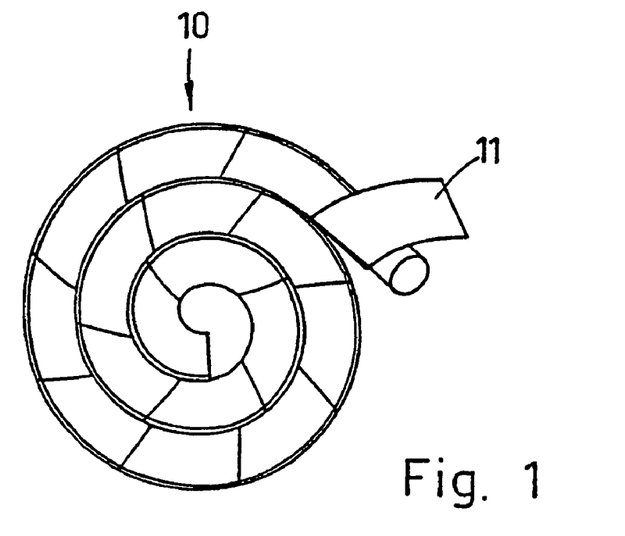
FIG. 1 illustrates in perspective view a section of a sealing barrier which is adhesive or coated with adhesive according to an embodiment of the invention.

FIG. 1 schematically illustrates an adhesive barrier 10 according to an embodiment of the invention, which barrier is constituted by a ribbon of plastic coated with any adhesive matter such as para or pale crepe rubber or poly(alkyl-acrylate) as described in "*Remington's Pharmaceutical Sciences*", Mack Publishing Company, 1990, page 1898, and other similar manuscripts, covered by a film 11 which protects said adhesive matter and is removed prior to the utilization of said barrier. Said barrier having, in the embodiment illustrated, a circular cross-section. Other cross-sections can of course be used and, as explained hereinafter, in some embodiments the barrier may be hollow or tube-like.

The barrier may consist of any material that is flexible and preferably sufficiently plastic and manageable to be used as explained hereinafter, and that is adhesive to the sealing film, hereinafter described, and adhesive, conforms and seals to skin irregularities and non-irritant and in general harmless to the human skin. An example of such a material is a biocompatible adhesive gel (such as RTV silicon or thick Vaseline paste). Alternatively, as has been said, the barrier may consist of a flexible, non-adhesive material, coated with an adhesive layer. An example of such a material is a soft, 3–10 millimeter thick foam cord, strip or band, of any suitable material, such as rubber, polyisoprene, RTV or silicon, coated with a thick layer of adhesive, such as described hereinbefore. Barriers made of such materials intimately conform to any skin irregularities and may surround any desired shape or size of affected surface.

Figure 2:
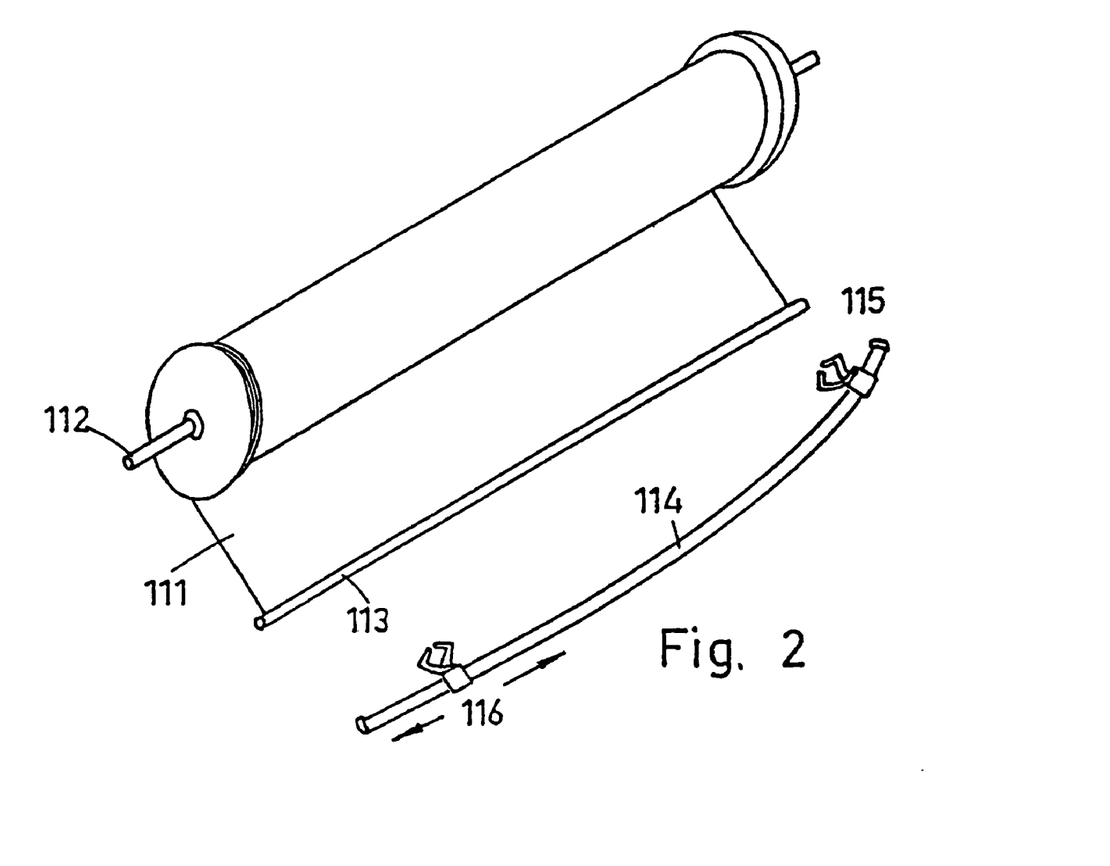
FIG. 2 illustrates in perspective view a portion of a sealing film according to the invention.

FIG. 2 schematically illustrates a film spreader which an impermeable, sealing film 111 in the form of a rolled sheet.

The film can be made of any impermeable, preferably but not necessarily transparent, material, e.g., a synthetic polymer such as Saran, polyurethane, nylon or polyethylene.

Said film may further consist of an electrically conductive material such as aluminum foil or carbon/metal impregnated plastic sheet. The roll of the film may for instance be rolled around a central rod 112, or a bow 114 with two grasping clips at the ends 115 and 116, when 116 may slide along the bow shaft, and the free edge strengthened and straightened by a rigid back 113 that allows a single user to spread the film easily. The bow with the clips may be replaced by any other rigid grasping rod or forceps that holds the free edge of the film.

The components of the occlusive dressing system are used to create an occlusive dressing in the following manner:

(a) A first end of the endless elongated flexible adhesive barrier is placed close to the wounded or other affected area (the terms "wound" or "wounded area", as used hereinafter, should be construed as comprising any area which it is desired, for any reason—not necessarily the presence of a wound—to enclose to protect or treat with the occlusive dressing), preferably at the periphery thereof, and is placed around and preferably close to said periphery until it completely encircles it; it is then cut (though, of course, it could have been cut before putting it in place):
  i) to a length appropriate to enable the cut end to be juxtaposed to said first end of said barrier, and the two ends are joined by pressing one to another lightly; or
  ii) to a slightly greater length thereof to enable the cut end to lay side by side juxtaposed to said first end of said barrier, and the two ends are joined by pressing one to the other lightly;
  iii) or in the case of an adhesive barrier materials such as putty or paste, RTV silicon or thick Vaseline paste they can be squeezed-extracted from their tube or syringe like container and spread in an abundant quantity (more than 1 cc. for a length of 1 cm. of the barrier) to encircle completely the desired area and constructing the adhesive barrier, thus forming a continuous, closed configuration surrounding the wounded area and generally a borderline area extending to some extent beyond said wounded area (the area thus surrounded by said closed configuration will be called hereinafter "the occluded area"). In some cases, when the wounded area is too large, said barrier may border only part of the affected area crossing the wounded area and occluding only part of the entire area.

(b) A portion of an impermeable sealing film, large enough completely to overlap the occluded area, generally separated from a film supply, such as a roll thereof, is superimposed to said barrier by spreading it manually or by using a specially designed "film spreader" and film container. As said, the film may be contained in a container that will allow it to roll out by pulling its free edge while holding the container. The container may contain or be replaced by a central pole around which the roll of the film can rotate. The free edge of the film can be strengthened with a rigid spreading back on an arc or bow with two grasping clips or a long jawed forceps that permits its orderly spreading using one hand. The container's edge at the film opening may be serrated or sharpened to permit its cutting. The cutting of the film from the entire roll may be eased by a small roller that while traveling along the serrated or sharpened edge cuts the film. Two rigid spreading backs may be used consecutively if more than one area should be covered. In this case one forceps-like rigid back is secured to the opening of the film container, the film passing through the jaws is held by the other similar forceps-like spreader and pulled out. To cut off the film one may use the serrated jaws of the spreader, a roller traveling along the holding jaws or any other cutting, shearing or perforating means along the jaw that is secured to the film container. The freed spreader is then inserted behind the first spreader (secured to the container) that becomes the spreader that will pull out the film.

The film is pressed lightly onto the adhesive barrier, thus pressing the latter onto the skin surface or other surface that it is wished to protect by means of the dressing. The film adheres to the barrier and the barrier adheres to said surface, whereby the occluded area is occluded essentially completely. The adhesive barrier and the film itself should not interfere or react in an undesirable manner with the patient's skin or other substances within the occluded area or with operations carried out therein. The complete seal of the occluded area allows to apply to it any form of medicines or substances, even liquids and gases.

Figure 3:
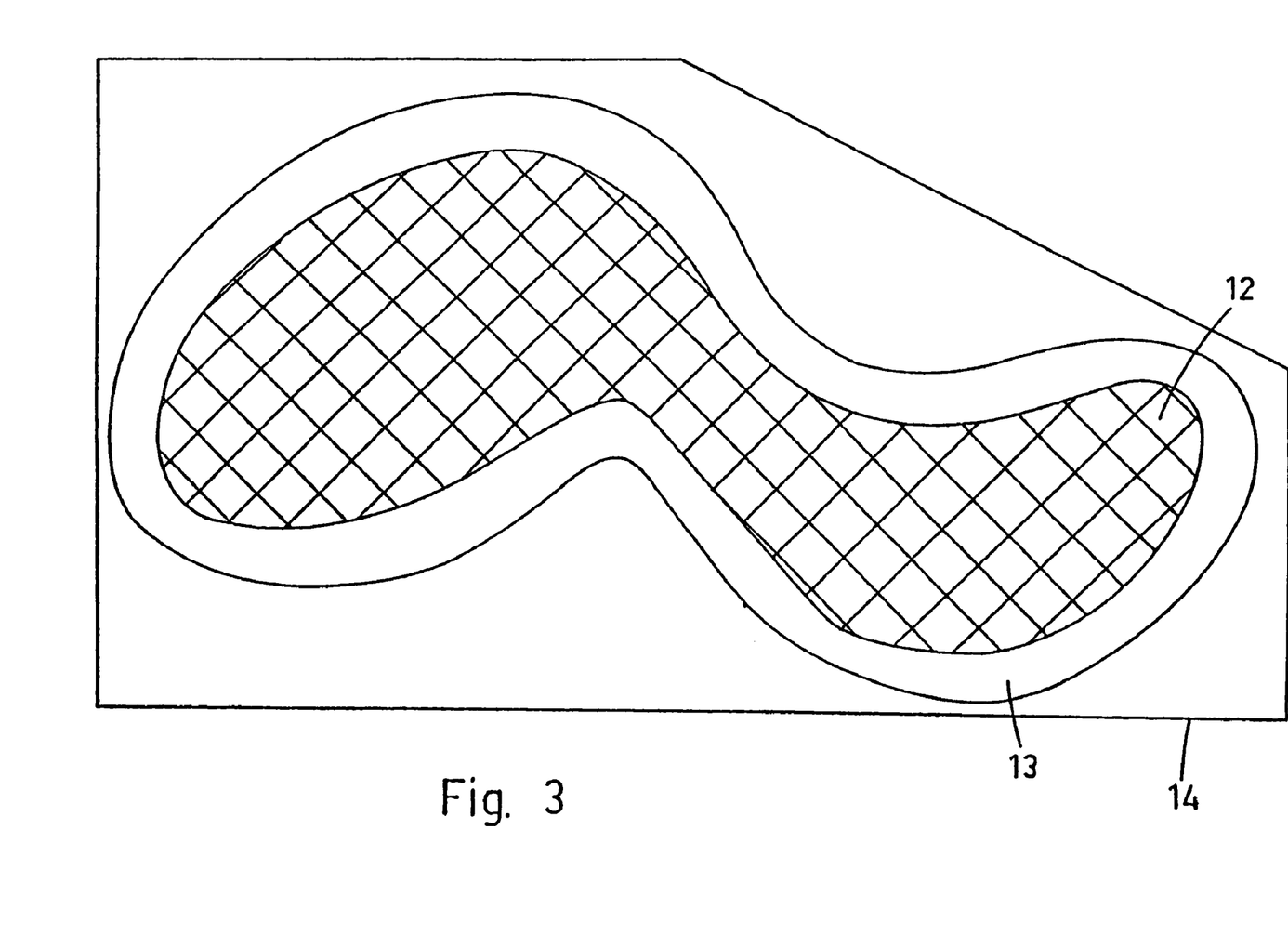
FIG. 3 schematically illustrates, in top, plane view, a dressing according to one embodiment of the invention, applied to the wound or other affected area.

A dressing resulting from a dressing system according to an embodiment of the invention is illustrated in FIG. 3. FIG. 3 is a top, schematic view, illustrating an occlusive dressing placed around a wound or a burn of an irregular shape. Shaded area 12 represents a wound or burn. Numeral 13 indicates the adhesive barrier and outer line 14 represents the outer limits of the sealing film which is adhered to adhesive barrier 13.

Any number of specially designed inlet and/or outlet valves may be placed at any point along the adhesive barrier, whereby to allow to introduce any desired substances or electrical or other probes into the space circumscribed at the periphery by the barrier and between the wounded area and the film, (hereinafter, "the occluded space") and/or to dilute, exchange or replace the contents of said occluded space. Said valves may be separate from the adhesive barrier and be connected with it when the dressing is applied, or may be integral with it or built-in, viz. constitute a component of the barrier. The insertion of a separate valve in the dressing through the barrier or the film may require the assistance of an adapter, unless the barrier is thick or flexible enough for a valve conduit to pass through it without interfering with the barrier's function. The valves may allow a continuous flow of any fluid, including thin or thick and more or less viscous liquids and/or gases over the desired occluded area. The valves may be one- or two-way valves and may be closed, if so desired, to maintain the occluded contents unchanged.

Low (vacuum) or high pressure pumps may be connected to the valves controlling the inside pressure or partial gases pressure. Electrical sources, to provide electrical current between the occluded materials and the patient's body, may be added to form an ionophoresis chamber or magnetic fields. The nature, structure and positioning of these valves and adapters should not interfere with the occluding properties of the adhesive barrier and/or of the sealing film, and of the whole occluding dressing.

Figure 4:
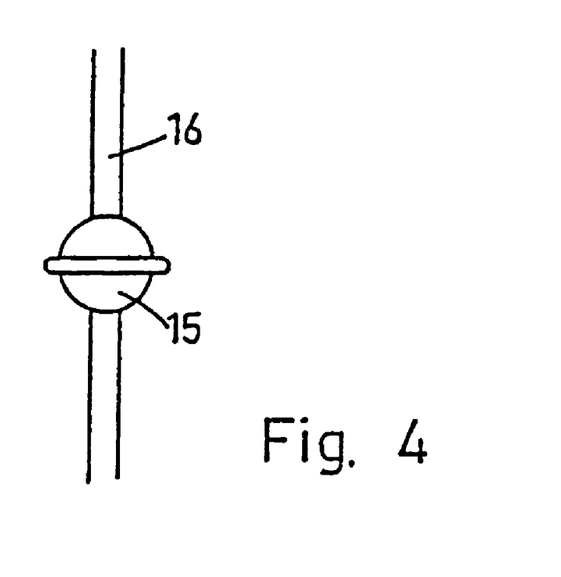
FIG. 4 schematically illustrates in plane view a valve applicable to an adhesive barrier according to the invention.
Figure 5A:
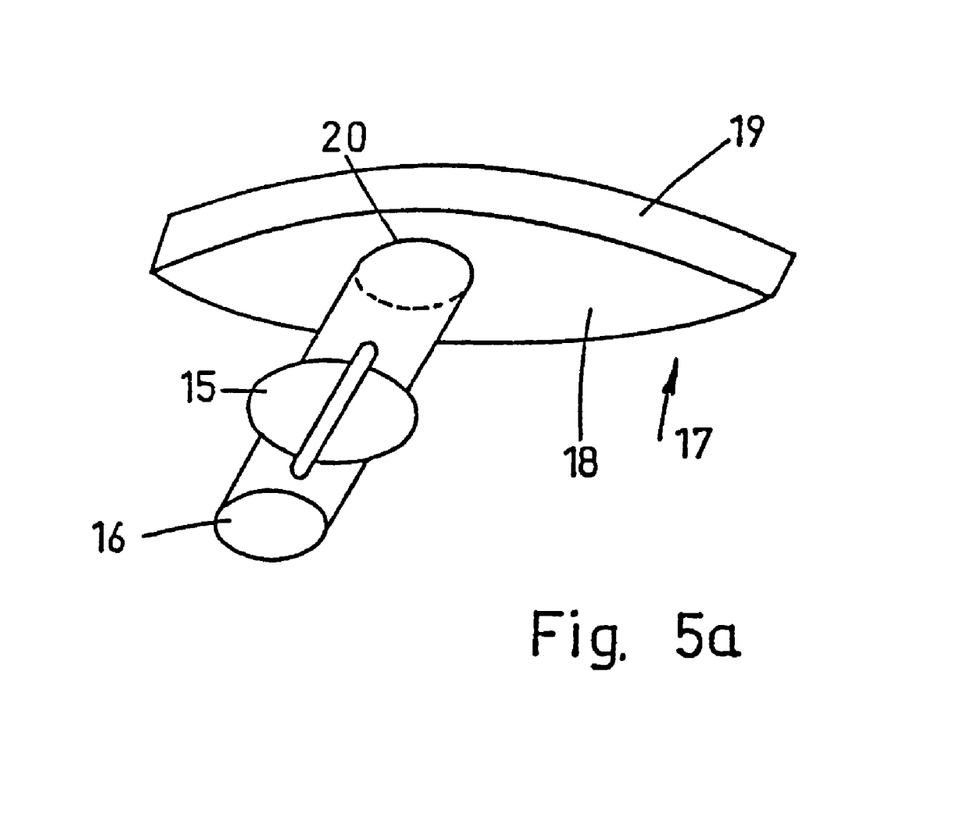
FIG. 5a is an adapter for the port passing under or over the sealing barrier.
Figure 5B:
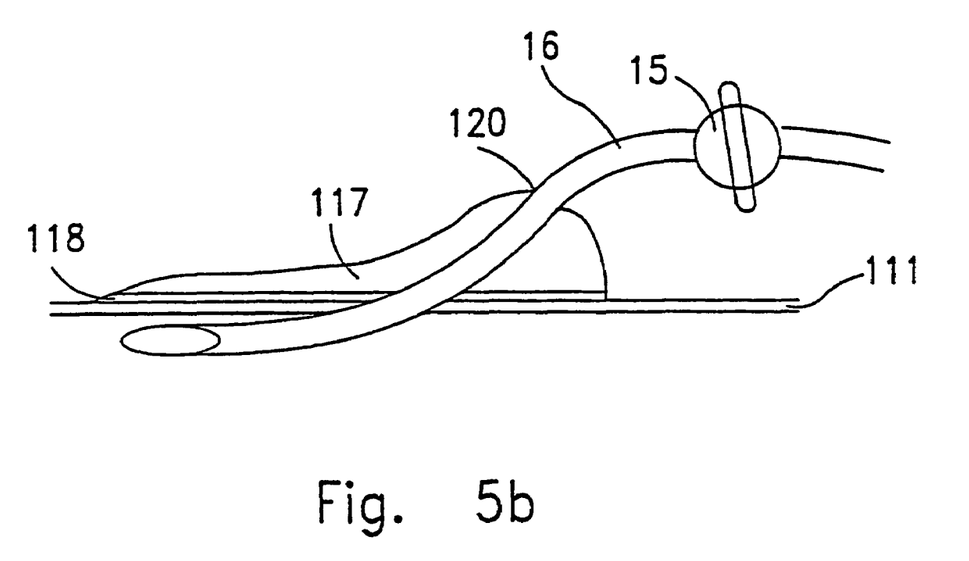
FIG. 5b illustrates the application of a valve or port through a flat adapter to the sealing film itself.

FIGS. 4 and 5 illustrate a valve 15, separate of the adhesive barrier, having a conduit 16, and an adapter 17 therefor, respectively. Adapter 17 has a substantially flat or moderately curved side 18, which is to be placed along the periphery of the occluded area, and a preferably curved side 19, which is to contact the adhesive barrier. Further, it has an opening 20 through which conduit 16 passes.

Figure 11A:
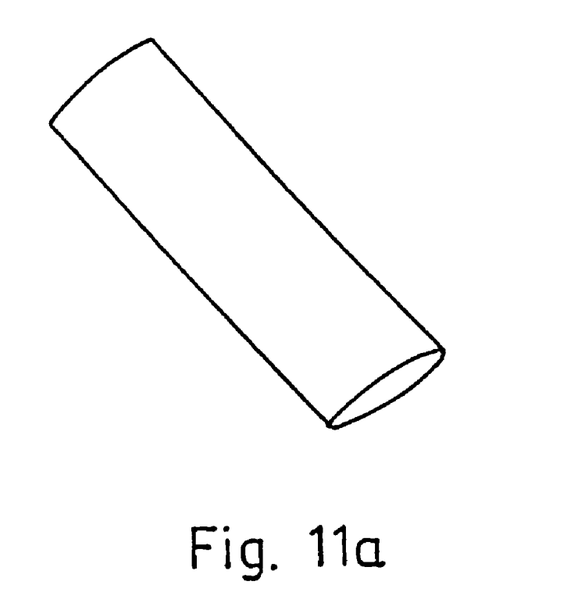
FIG. 11a illustrates in schematic perspective view a portion of a conduit according to the invention, made of two sheets of plastic material welded at the seam.
Figure 11B:
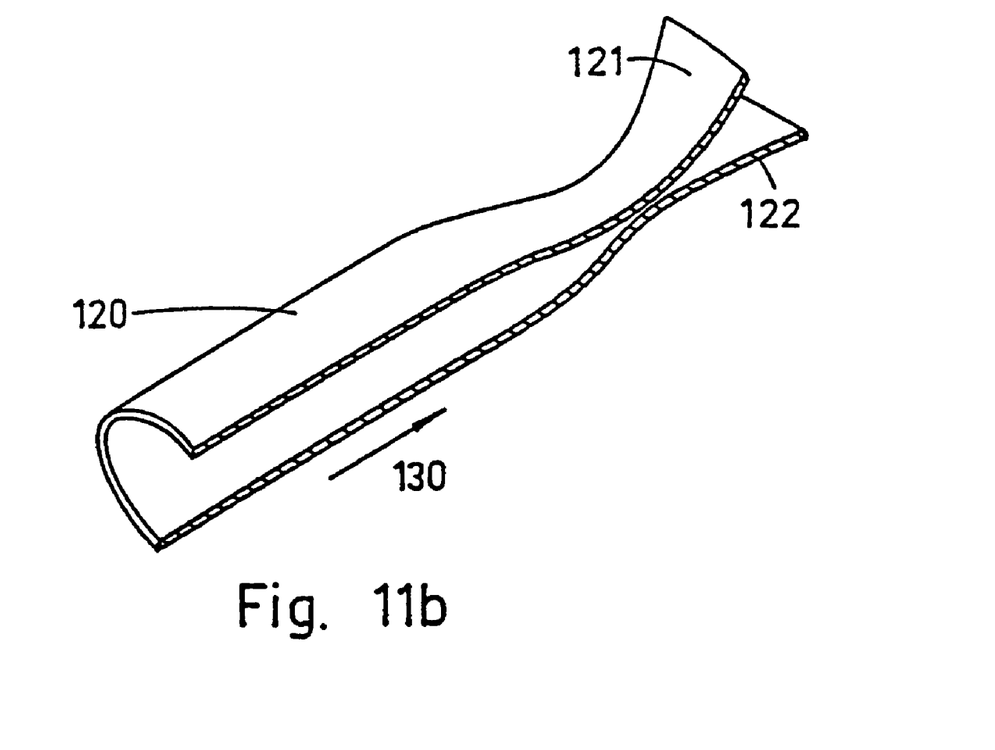
FIG. 11b illustrates in schematic partial cross-section a leaf valve according to an embodiment of the invention that may be made of two flexible plastic sheets welded together.

An additional embodiment of a conduit is illustrated in FIG. 11a in a schematic perspective view. Said conduit consists of two plastic strips welded to each other along both of each of their ends, to form a flat conduit and a leaf valve. Said conduit is coated on its outside surfaces by a layer of adhesive. Thus, said conduit may be placed onto the skin and pressed lightly thereto, prior to the placement of the occlusive dressing as described above.

An additional embodiment of a valve according to the invention is a leaf valve which is well known in the art. An example of such a leaf valve is illustrated in FIG. 11a in a schematic partial cross-section. Said valve consists of a conduit 120, inside which are two flaps 121 and 122. Said flaps are connected at their ends to the inside surface of said conduit, on two opposite sides, one on each side, and their free end are both positioned in the same direction, roughly parallel to the length axis of said conduit. Thus, upon applying pressure on flowing matter in the direction of the arrow, a passage may open between said flaps and matter can flow through the conduit in said direction. Upon applying pressure on flowing matter in the opposite direction to said arrow, said matter forces said flaps one towards the other to form a closure of passage which prevents the flow of said matter through said conduit beyond the position of said flaps.

FIG. 5b illustrates an adapter for a conduit or a valved port to be placed on top of the occluding film instead of passing through the barrier. Said adapter connects and directs, seals and stabilizes the passage of the conduit tangentially through the film.

Figure 6A:
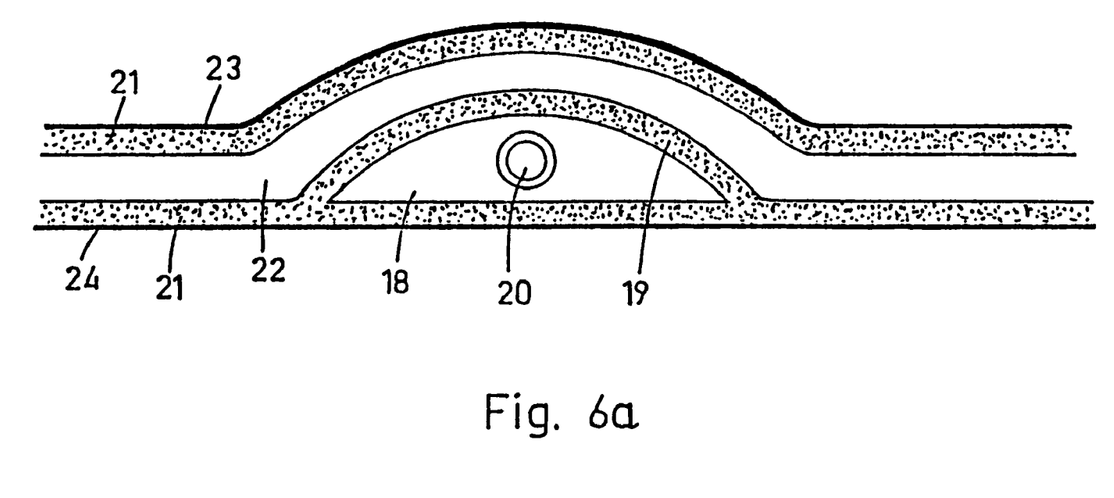
FIG. 6a illustrates in schematic partial cross-section a dressing according to an embodiment of the invention applied to a skin surface.

FIG. 6a illustrates the resulting assembly in cross-section perpendicular to the occluded area. In this embodiment, the adhesive barrier is not made of an adhesive material, but is coated with a layer of adhesive 21 over a non-adhesive body 22. Such a coating may be omitted on side 19, if the adhesive properties of the adhesive barrier are sufficient to seal it against the adapter. The sealing film is shown at 23, and the surface of the skin at 24. The remaining numerals are the same as in FIGS. 4 and 5.

Figure 6B:
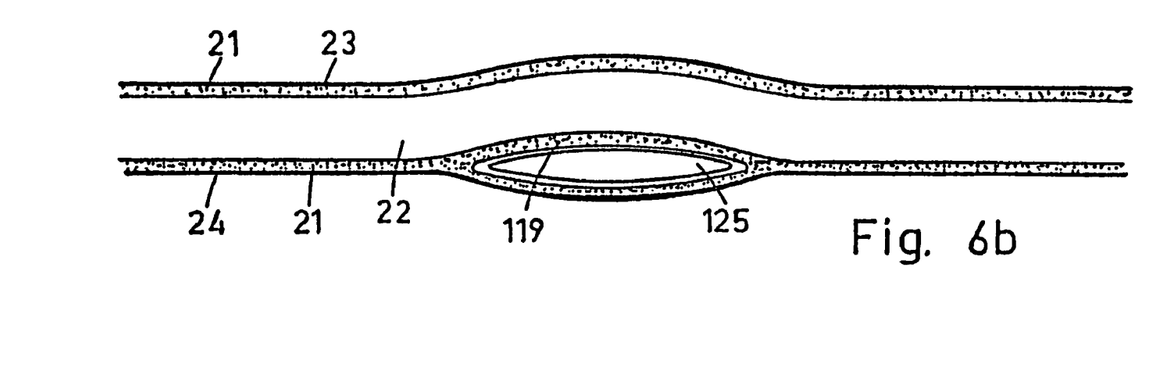
FIG. 6b illustrates in schematic partial cross-section a dressing according to an embodiment of the invention applied to a skin surface.

FIG. 6b illustrates similarly to FIG. 6a the resulting assembly in cross-section perpendicular to the occluded area. The flat conduit is shown at 125, and a layer of adhesive 119 between the barrier and the conduit may be coated on the barrier, on the conduit, on both the barrier and the conduit, or said layer may be omitted if the adhesive properties of the adhesive barrier are sufficient to seal it against the conduit. The remaining numerals are the same as in FIG. 6a.

Figure 7:
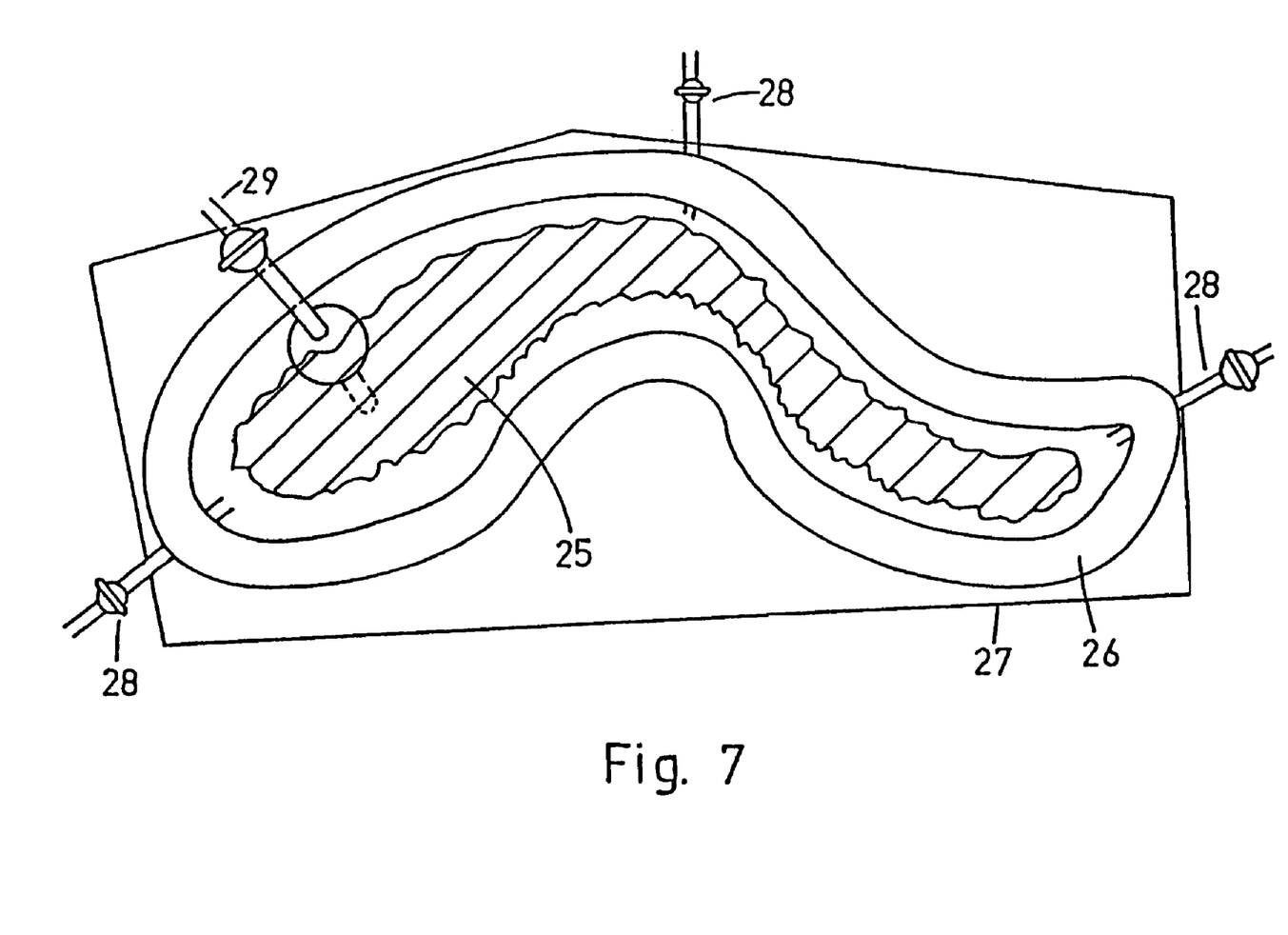
FIG. 7 is a schematic top, plane view similar to that of FIG. 3, but illustrating another embodiment of the invention.

FIG. 7 is a top view illustrating an occlusive dressing system placed around a wound or burn of an irregular shape, wherein shaded area 25 represents a wound or burn, 26 indicates an adhesive barrier, line 27 represents the outer edge of the sealing film and numeral 28 indicates valves connected to the adhesive barrier or the film 20, optionally by means of adapters, not shown in the drawing.

Figure 8A:
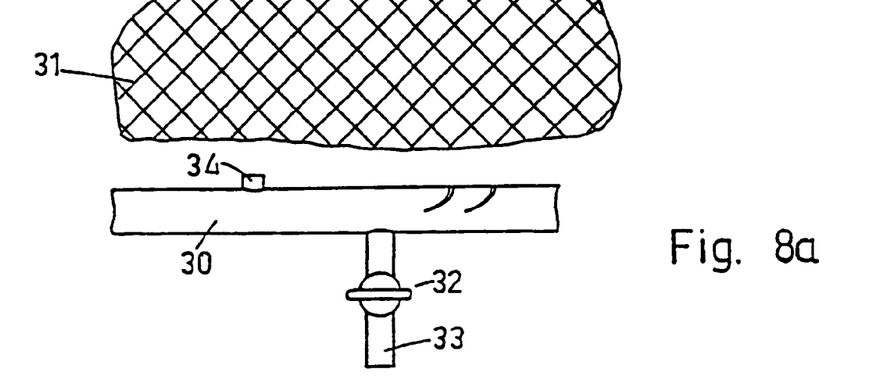
FIGS. 8a, 8b and 8c schematically and fragmentarily illustrate another embodiment of the invention, respectively in plane view, in perspective view from the outside of the wound or affected area and from the inside thereof.
Figure 8B:
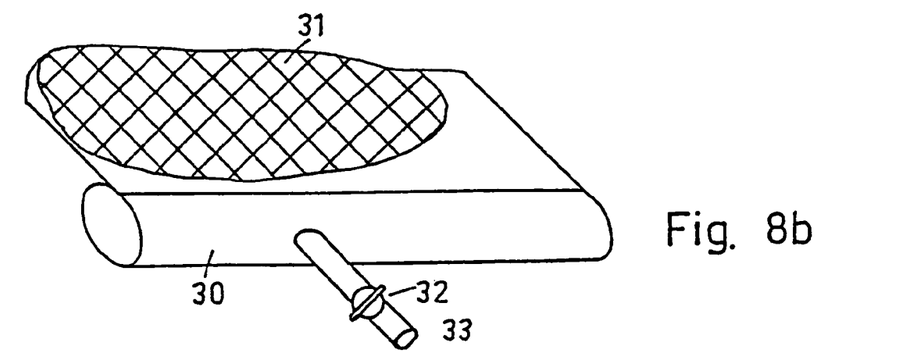
Figure 8C:
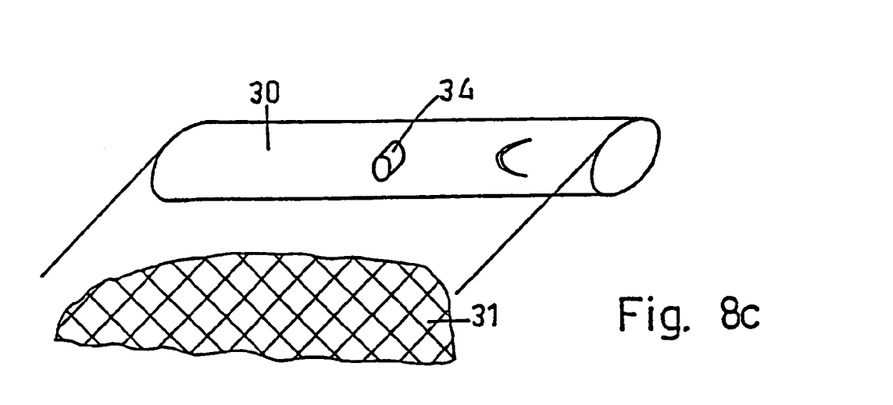
Figure 8D:
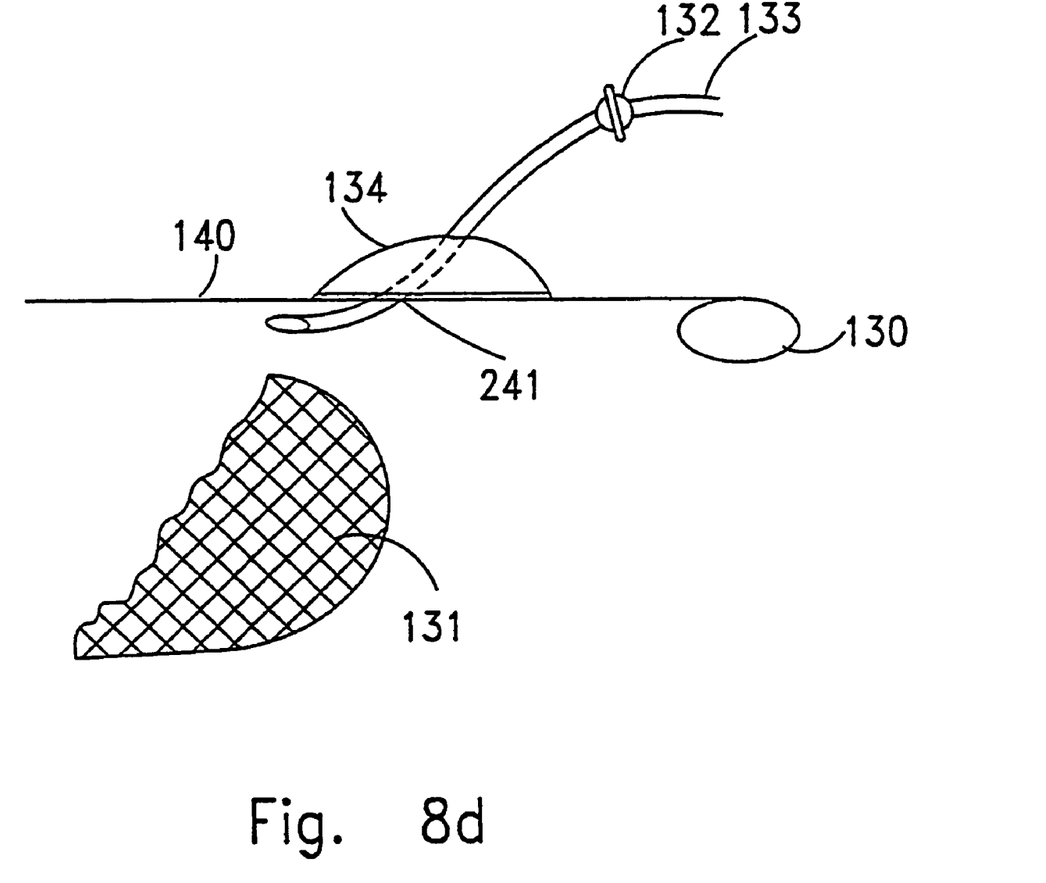
FIG. 8d is an adapter for a conduit or a valved port to be placed on top of the occlusive film instead of passing through the barrier.

FIGS. 8a, 8b and 8c illustrate a segment of an endless, elongated, flexible adhesive barrier 30 which comprises valves that are integral therewith, viz. are components thereof. Numeral 31 indicates the wounded area, and 32 a valve having a conduit 33 with an outlet 34. These outlets may be in the form of semi-circular flaps incised into the tube forming valve-like flaps. FIG. 8a is a fragmentary top view of said barrier 30, which is hollow and tube-like, as seen in FIGS. 8b and 8c. FIG. 8b is a fragmentary perspective view from above and outside the occluded area looking inwards and FIG. 8c is a fragmentary perspective view from above and inside the occluded area looking outwards. FIG. 8d illustrates an adapter for a conduit or a valved port to be placed on top of the occluding film instead of passing through the barrier.

Figure 9A:
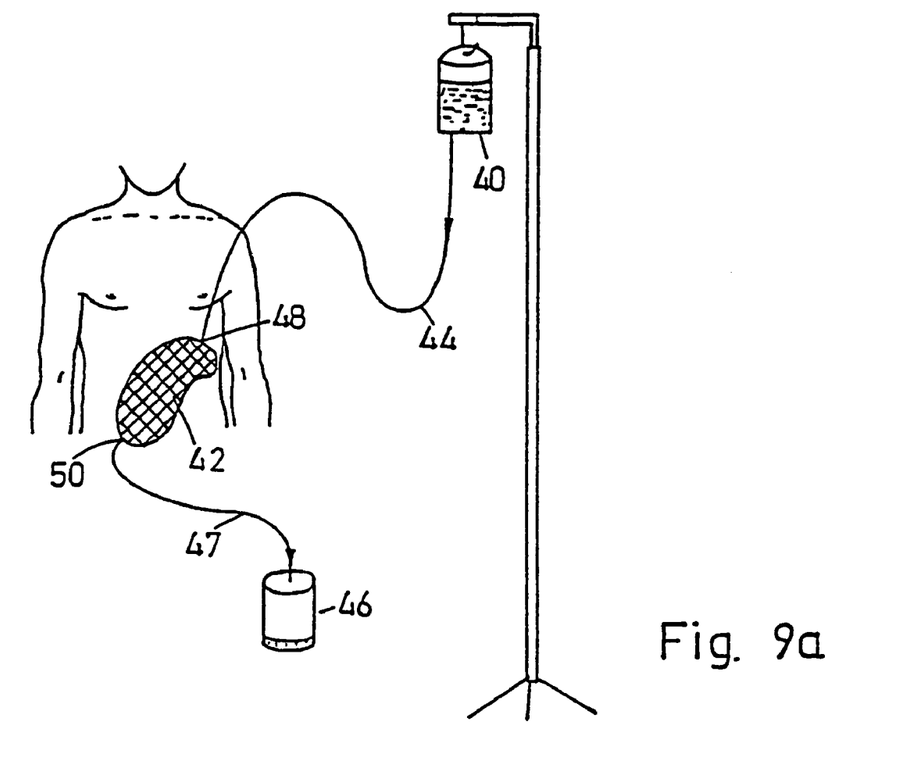
FIGS. 9a and 9b schematically illustrate two systems for modifying the atmosphere in the space between the occlusive dressing and the affected area according to embodiments of the invention.
Figure 9B:
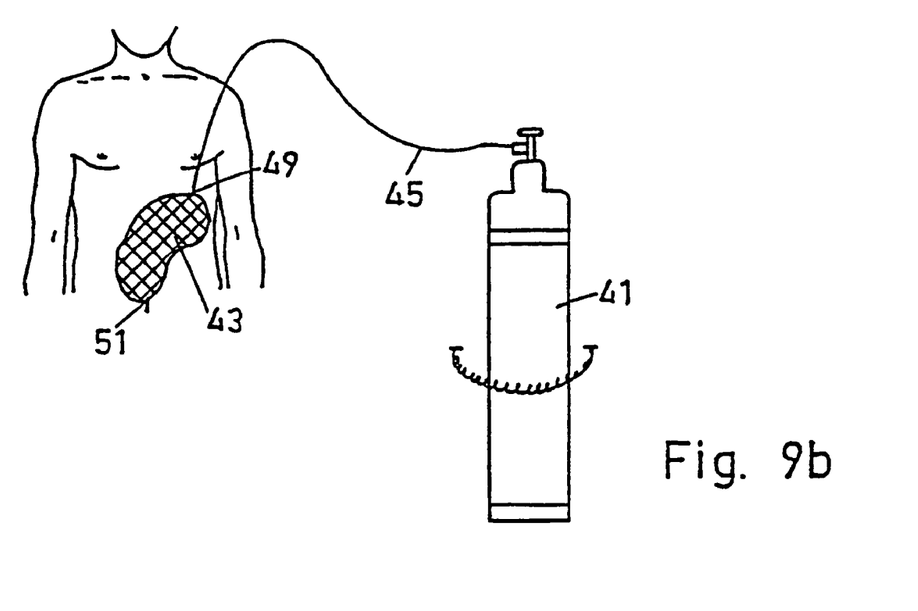

FIGS. 9a and 9b illustrate the use of a dressing system according to the invention for introducing and eliminating fluids or gases through valves into and from the occluded space. Numeral 40 indicates a source of non-gaseous fluid; numeral 41 indicates a gas source; numerals 42 and 43 indicate dressings; numerals 44 and 45 indicate ducts leading from said non-gaseous fluid source and gas source, respectively, to said dressings; numeral 46 indicates a disposal container; numeral 47 indicates a duct leading from dressing 42 to disposal container 46; numerals 48 and 49 indicate inlet valves into the occluded spaces of dressings 42 and 43; and numerals 50 and 51 indicate free openings or outlet valves from the occluded spaces of dressings 42 and 43. The gas source 41 may be replaced by a vacuum pump that creates a lower atmospheric pressure inside the dressing. The vacuum may be adjusted to high or low, continuous or alternating.

Figure 9C:
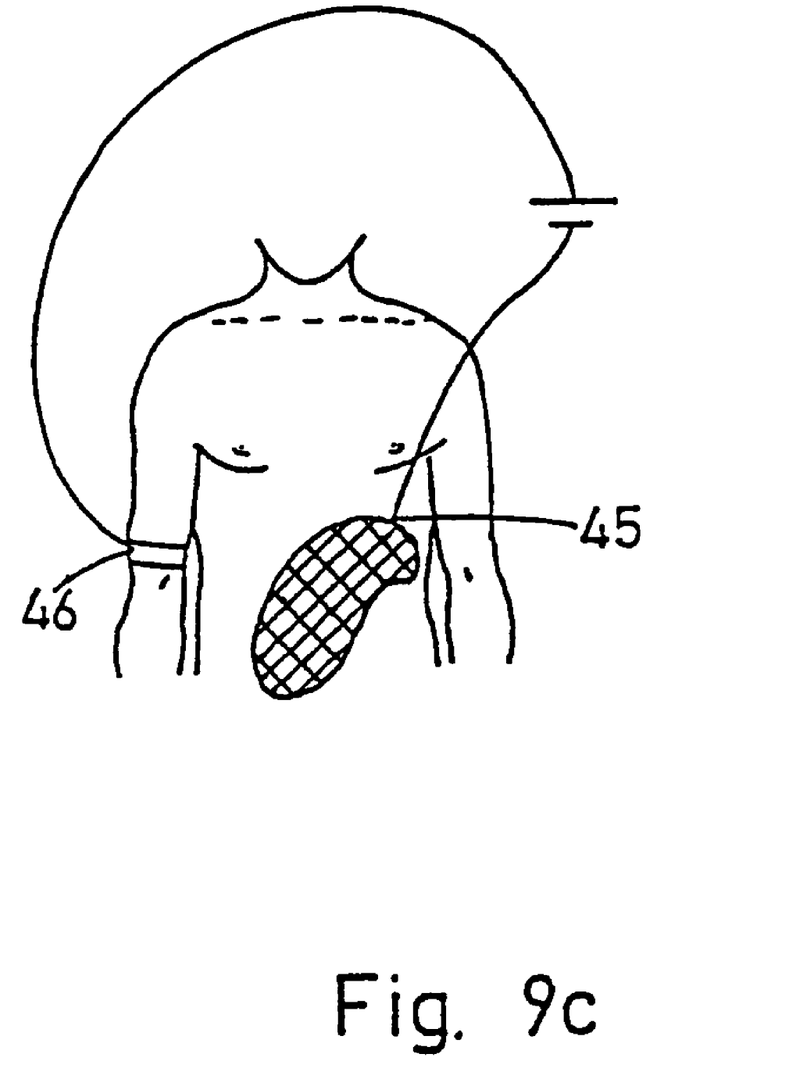
FIG. 9c schematically illustrates a systems for changing the electrical field in the wound and permitting controlled ionophoresis.

FIG. 9c illustrates the use of a dressing system according to the invention for providing an electrical field at the occluded area. Numeral 45 indicates an electrode passing through an inlet tube and numeral 46 indicates another electrode placed on the patient's body to close the circuit with the electrical or magnetic source. When using a conductive film, electrode 45 may be connected directly to the film, and the barrier should have electrical isolation properties thus, the electrical field being established between the film and the body (electrode 46).

Figure 10:
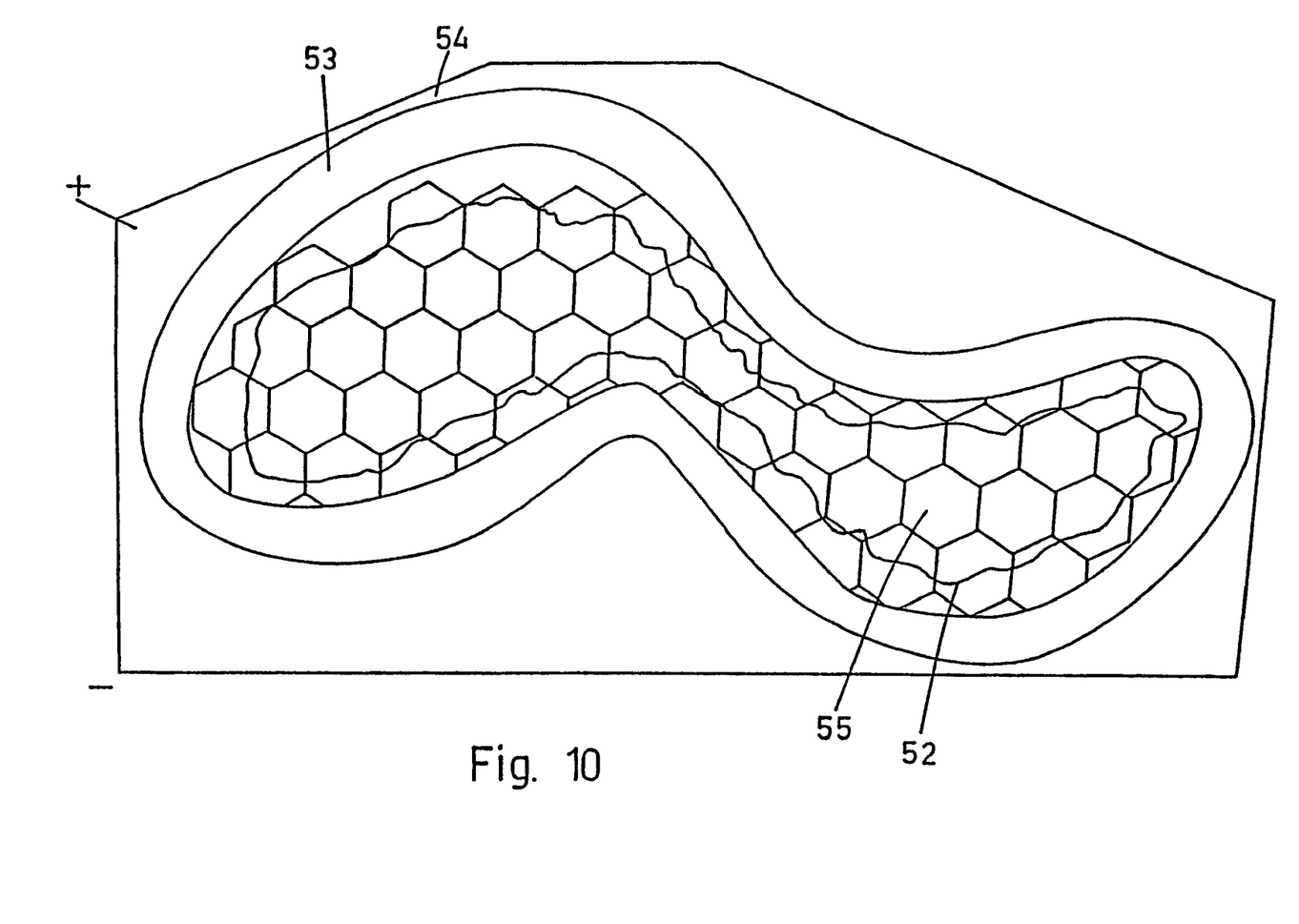
FIG. 10 is a top, plane view similar to FIG. 3 but illustrating another embodiment of the invention.

FIG. 10 is a top view illustrating an occlusive dressing placed around a wound of an irregular shape, wherein numeral 52 represents the boundary of a wound, 53 is the adhesive barrier and the outer line 54 represents the outer edge of the sealing film which is adhered to the adhesive barrier. The hexagonal areas 55 represent stabilizing and carrier matrices, hereinafter described.

The dressing system according to the invention, being a general, multipurpose device, may include several additional features specifically designed to develop or enhance certain of its properties. Such features may include stabilizing and carrier matrices. Thus, medicines or materials with such a consistency that they do not stick and remain on the site of application, but allows them to slide downwards following the body curvatures, may be contained in a stabilizing or carrier matrix. These matrices, containing any number of desired bio-active components, could be placed on the treatment site, covered with the occlusive dressing and activated by infusing the appropriate activating liquids (such as solvents and irrigation liquids) through the inlet valves.

Said matrices may be in the form of fibrous nets, fibrous knotted nets, gauze, non-wovens, sponges or honeycomb or any other acceptable form and may be made of natural or synthetic, stable or degradable material, such as those described in "*Remington's Pharmaceutical Sciences*", Mack Publishing Company, 1990, pages 1895–1900 or other similar source manuscripts.

An electrophoretic releasing system may also be provided in a dressing according to the invention. In this system that is well known in the art, one electrical pole is connected to the occluded material and the other electrical pole is connected to the patient's body. Electrical current passing between the poles cause the transfer of ions or materials according to their electrical charges. The above phenomenon is known as ionophoresis.

The nature and structure of the aforementioned matrix material may be such as to absorb and direct the flow of the medicines and the solvents or irrigation fluids to the desired treatment target. It is possible to use this system as a time or quantity controlled release system, by changing the nature and density of the medicating substances and their solvents according to the change of the nature and structure of the matrices in order to use well known forces such as surface tension hydrophilic or hydrophobic forces or electrical field.

Electrical fields may be used also to control the movement of electrically charged molecules or particles to the desired treatment site. For this purpose one electrical pole is connected to the sealing film or carrier matrix and the other to the patient body. This electrophoretic releasing and transportation system, known also as "ionophoresis system", helps to direct the desired medicaments to their targets and the occluding dressing of the invention is well designed to serve as such an electrophoretic chamber.

The following non-limitative examples illustrate some embodiments of the invention.

As will be appreciated by the skilled person, the invention can be exploited by using a very great variety of materials. For instance, the impermeable sealing film may be a saran, polyurethane, nylon or polyethylene film. The carrier matrix may be, e.g., a fibrous net, such as the Kerlix knotted net (manufactured by Knoll and others), or a 4×4-8 ply gauze (manufactured by Johnson & Johnson), or a Softwick nonwoven surgical sponge (also by Johnson & Johnson and others), or a Nu-Gauze surgical sponge. Furthermore, the matrix may have different shapes, e.g., it may be honeycomb or hexagonal. Several different adhesives can be used, such as para or pale crepe rubber, poly isobutylene or polymethacrylate. Thus, as will be apparent to the skilled person, although illustrative and non-limitative examples of suitable materials have been given above, for the purpose of illustration, the invention is by no means limited to such or other materials and many occlusive dressing systems can be provided in many ways, without exceeding the scope of the invention.

The invention claimed is:

1. An occlusive dressing system, comprising a closed barrier consisting of a length of a flexible, adhesive barrier, the length having two ends, surrounding an afflicted area and having its two ends adhesively connected, and a portion of an impermeable sealing film superimposed to and pressed against said closed barrier, said closed barrier and said film forming a gas-tight seal.

2. The occlusive dressing system according to claim 1, further comprising means for providing a communication through the dressing with the external environment.

3. The occlusive dressing system according to claim 2, wherein the means for providing communication between the external environment and the afflicted area comprises at least one valve connected to a conduit which has an inlet/outlet into said afflicted area.

4. The occlusive dressing system according to claim 3, wherein the at least one valve is separate from the barrier and the sealing film.

5. The occlusive dressing system according to claim 3, wherein the at least one valve is an integral component of the barrier or the sealing film.

6. The occlusive dressing system according to claim 3, further comprising at least one adapter for permitting insertion of the conduit means through the barrier or the sealing film.

7. The occlusive dressing system according to claim 3, further comprising a chemical or an electrical releasing system.

8. The occlusive dressing system according to claim 1, wherein the barrier consists essentially of an adhesive material.

9. The occlusive dressing system according to claim 8, wherein the adhesive material is a biocompatible adhesive selected from the group consisting of gel, paste and putty.

10. The occlusive dressing system according to claim 1, wherein the barrier comprises flexible, non-adhesive material, coated with an adhesive layer.

11. The occlusive dressing system according to claim 10, wherein the adhesive layer is a material selected from the group consisting of para crepe rubber, pale crepe rubber, one or more polymers or isobutylene, and poly(alkyl-acrylate).

12. The occlusive dressing system according to claim 1, wherein the sealing film comprises a synthetic polymer.

13. The occlusive dressing system according to claim 12, wherein the synthetic polymer is selected from the group consisting of polyvinylidene chloride, polyurethane, nylon and polyethylene.

14. The occlusive dressing system according to claim 1, wherein the sealing film is electrically conductive.

15. The occlusive dressing system according to claim 1, wherein the sealing film is supplied in a roll of film.

16. The occlusive dressing system according to claim 1, wherein the barrier has a circular cross section.

17. The occlusive dressing system according to claim 1, wherein the adhesive barrier is selected from the group consisting of ribbons of plastic coated with adhesive matter, thick foam cords coated with adhesive matter and biocompatible adhesive gels.

18. A method of making an occlusive dressing over a body area comprising an afflicted area, which comprises:
   a) providing an elongated, flexible, adhesive barrier, having a given length with two ends;
   b) providing a film having more than one portion;
   c) encircling the length of the barrier about a body area such that the two ends meet;
   d) connecting the two ends of the length of barrier in (c) to form a closed configuration;
   e) separating from the film a portion thereof large enough to overlap the closed configuration;
   f) superimposing the film portion of (e) over said closed configuration; and
   g) pressing said film portion onto said closed configuration such that said film portion adheres to said closed configuration to form a gas tight seal and to form an occlusive dressing to the body area wherein at least part of the circumscribed body area does not contact the adhesive barrier upon formation of the occlusive dressing.

* * * * *